(12) United States Patent
Boiko et al.

(10) Patent No.: US 10,729,368 B1
(45) Date of Patent: Aug. 4, 2020

(54) COMPUTER SYSTEMS AND COMPUTER-IMPLEMENTED METHODS FOR PSYCHODIAGNOSTICS AND PSYCHO PERSONALITY CORRECTION USING ELECTRONIC COMPUTING DEVICE

(71) Applicant: Facemetrics Limited, Nicosia (CY)

(72) Inventors: Mikhail Boiko, Cracow (PL); Aleh Arol, Minsk (BY); Dzianis Pirshtuk, Minsk (BY); Aliaksandr Vinahradau, Minsk (BY); Alex Glinsky, Minsk (BY); Pavel Kavaliou, Minsk (BY)

(73) Assignee: Facemetrics Limited, Nicosia (CY)

( * ) Notice: Subject to any disclaimer, the term of this patent is extended or adjusted under 35 U.S.C. 154(b) by 0 days.

(21) Appl. No.: 16/522,186

(22) Filed: Jul. 25, 2019

(51) Int. Cl.
| | |
|---|---|
| *G06K 9/00* | (2006.01) |
| *A61B 5/16* | (2006.01) |
| *A61B 5/00* | (2006.01) |
| *G16H 50/20* | (2018.01) |
| *G06N 3/08* | (2006.01) |

(52) U.S. Cl.
CPC ............ *A61B 5/167* (2013.01); *A61B 5/0077* (2013.01); *A61B 5/486* (2013.01); *A61B 5/7267* (2013.01); *G06K 9/00255* (2013.01); *G06K 9/00302* (2013.01); *G06N 3/08* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 8,524,665 B2* | 9/2013 | Yurgelun-Todd | ............................ A61K 38/2235 514/1 |
| 2007/0048706 A1* | 3/2007 | Tan | .......................... G09B 7/00 434/236 |
| 2010/0189358 A1* | 7/2010 | Kaneda | .............. G06K 9/00744 382/195 |
| 2012/0002848 A1* | 1/2012 | Hill | ........................ G16H 50/20 382/118 |

(Continued)

OTHER PUBLICATIONS

Towards Evaluation of Phonics Method for Teaching of Reading Using Artificial Neural Networks (A Cognitive Modeling Approach), Hassan M. Hassan et al.,978-1-4244-1 835-0/07, IEEE, 2007, pp. 855-862 (Year: 2007).*

(Continued)

*Primary Examiner* — Jayesh A Patel
(74) *Attorney, Agent, or Firm* — Greenberg Traurig, LLP

(57) ABSTRACT

A computer-implemented method and system can include obtaining, by at least one processor, at least one visual input comprising a face of at least one person. The at least one processor can input the at least one visual input into at least one psychodiagnostic neural network (PNN) to obtain at least one personality metric of the at least one person. The at least one personality metric of the at least one person can include at least one personality dimension and at least one numerical personality score. The at least one numerical personality score may provide a numerical indication of the strength of a particular personality dimension and display at least one personality report on at least one screen of at least one computing device. The at least one personality report may include the at least one personality metric of the at least one person.

20 Claims, 4 Drawing Sheets

400
EXEMPLARY INPUTS AND OUTPUTS OF THE INVENTIVE NEURAL NETWORK ARCHITECTURE agreeableness 0.56293
conscientiousness 0.47317
extraversion 0.48275
interview 0.50121
neuroticism 0.58903
openness 0.80327 agreeableness 0.46967 conscientio
usness 0.46652 extraversion 0.3
8504 interview 0.38837 neurotici
sm 0.38262 openness 0.47
754

(56) References Cited

U.S. PATENT DOCUMENTS

| | | | | |
|---|---|---|---|---|
| 2012/0219934 A1* | 8/2012 | Nakane | ................ | G09B 19/00 |
| | | | | 434/236 |
| 2013/0102918 A1* | 4/2013 | Etkin | ................... | G09B 19/00 |
| | | | | 600/544 |
| 2013/0300650 A1* | 11/2013 | Liu | ....................... | G06F 3/011 |
| | | | | 345/156 |
| 2017/0213190 A1* | 7/2017 | Hazan | .................... | G10L 25/63 |
| 2017/0372189 A1* | 12/2017 | Joo | ................. | B60W 50/0098 |
| 2018/0046150 A1* | 2/2018 | Ooba | ................. | G05B 13/027 |
| 2018/0310841 A1* | 11/2018 | Khwaja | ............. | G06K 9/00315 |

OTHER PUBLICATIONS

Testing neural network models of personality, Michael Quek et al., ELSEVIER, 2006, pp. 700-706 (Year: 2006).*

Deep Learning based Personality Recognition from Facebook Status Updates, Jianguo Yu et al., 978-1-5386-2965-9/17, IEEE, 2017, pp. 383-387 (Year: 2017).*

Video-based emotion recognition in the wild using deep transfer learning and score fusion, Heysem Kaya et al., ELSEVIER, 2017, pp. 66-75 (Year: 2017).*

Evaluating attributed personality traits from scene perception probability, Hancheng Zhua et al., ELSEVIER, 2018, pp. 121-126 (Year: 2018).*

\* cited by examiner

300
EXEMPLARY NEURAL NETWORK ARCHITECTURE

| Layers | Output Size | DenseNet-121 | DenseNet-169 | DenseNet-201 | DenseNet-264 |
|---|---|---|---|---|---|
| Convolution | 112 × 112 | 7 × 7 conv, stride 2 | | | |
| Pooling | 56 × 56 | 3 × 3 max pool, stride 2 | | | |
| Dense Block (1) | 56 × 56 | [1 × 1 conv; 3 × 3 conv] × 6 | [1 × 1 conv; 3 × 3 conv] × 6 | [1 × 1 conv; 3 × 3 conv] × 6 | [1 × 1 conv; 3 × 3 conv] × 6 |
| Transition Layer (1) | 56 × 56 | 1 × 1 conv | | | |
| | 28 × 28 | 2 × 2 average pool, stride 2 | | | |
| Dense Block (2) | 28 × 28 | [1 × 1 conv; 3 × 3 conv] × 12 | [1 × 1 conv; 3 × 3 conv] × 12 | [1 × 1 conv; 3 × 3 conv] × 12 | [1 × 1 conv; 3 × 3 conv] × 12 |
| Transition Layer (2) | 28 × 28 | 1 × 1 conv | | | |
| | 14 × 14 | 2 × 2 average pool, stride 2 | | | |
| Dense Block (3) | 14 × 14 | [1 × 1 conv; 3 × 3 conv] × 24 | [1 × 1 conv; 3 × 3 conv] × 32 | [1 × 1 conv; 3 × 3 conv] × 48 | [1 × 1 conv; 3 × 3 conv] × 64 |
| Transition Layer (3) | 14 × 14 | 1 × 1 conv | | | |
| | 7 × 7 | 2 × 2 average pool, stride 2 | | | |
| Dense Block (4) | 7 × 7 | [1 × 1 conv; 3 × 3 conv] × 16 | [1 × 1 conv; 3 × 3 conv] × 32 | [1 × 1 conv; 3 × 3 conv] × 32 | [1 × 1 conv; 3 × 3 conv] × 48 |
| Classification Layer | 1 × 1 | 7 × 7 global average pool | | | |
| | | 1000D fully-connected, softmax | | | |

FIG. 3

400
EXEMPLARY INPUTS AND OUTPUTS OF THE INVENTIVE NEURAL NETWORK ARCHITECTURE
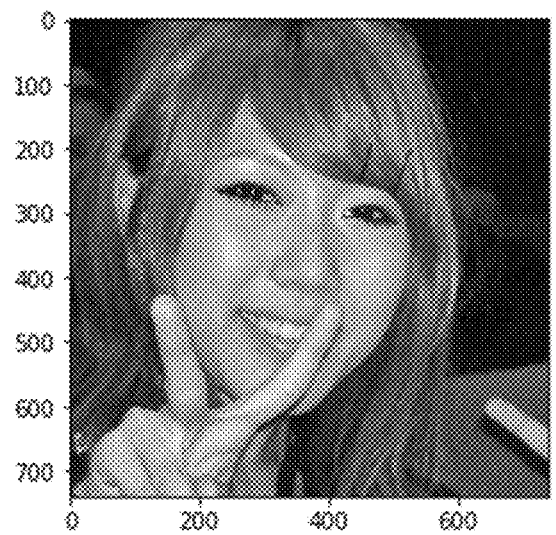
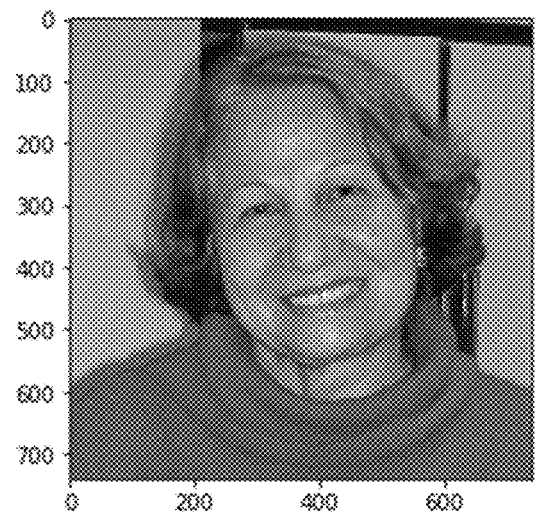
agreeableness 0.56293
conscientiousness 0.47317
extraversion 0.48275
interview 0.50121
neuroticism 0.58903
openness 0.80327
agreeableness 0.46967 conscientiousness 0.46652 extraversion 0.38504 interview 0.38837 neuroticism 0.38262 openness 0.47754
FIG. 4

COMPUTER SYSTEMS AND COMPUTER-IMPLEMENTED METHODS FOR PSYCHODIAGNOSTICS AND PSYCHO PERSONALITY CORRECTION USING ELECTRONIC COMPUTING DEVICE

COPYRIGHT NOTICE

A portion of the disclosure of this patent document may contain material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in drawings that form a part of this document: Copyright, Facemetrics Limited, All Rights Reserved.

FIELD OF TECHNOLOGY

The present disclosure generally relates to improved computer-based systems/methods and improved computing devices configured for psychodiagnostics and psycho personality correction during user interaction with electronic computing devices.

SUMMARY OF DESCRIBED SUBJECT MATTER

In some embodiments, the present disclosure provides an exemplary technically improved computer-based method that includes: obtaining, by at least one processor, at least one visual input comprising a face of at least one person; inputting, by the at least one processor, the at least one visual input into at least one psychodiagnostic neural network (PNN) to obtain at least one personality metric of the at least one person; wherein the at least one personality metric of the at least one person comprises: at least one personality dimension, and at least one numerical personality score, wherein the at least one numerical personality score provides a numerical indication of the strength of a particular personality dimension; and displaying at least one personality report on at least one screen of at least one computing device; wherein the at least one personality report comprises the at least one personality metric of the at least one person.

In some embodiments, the present disclosure provides an exemplary technically improved computer-based system that includes: a camera component, wherein the camera component is configured to acquire at least one visual input comprising a face of at least one person, at least one processor; a non-transitory computer memory, storing a computer program that, when executed by the at least one processor, causes the at least one processor to: input the at least one visual input into at least one psychodiagnostic neural network (PNN) to obtain at least one personality metric of the at least one person; wherein the at least one personality metric of the at least one person comprises: at least one personality dimension, and at least one numerical personality score, wherein the at least one numerical personality score provides a numerical indication of the strength of a particular personality dimension; and display at least one personality report on at least one screen of at least one computing device; wherein the at least one personality report comprises the at least one personality metric of the at least one person.

In some embodiments, the at least one visual input comprises at least one video frame, at least one image, or both.

In some embodiments, a particular personality metric of the at least one personality metric is at least one of: at least one psychotype according to Briggs Myers, at least one personality trait according to the Big 5, a compatibility score, a score evaluating the at least one person in a particular situation, or a combination thereof.

In some embodiments, a particular personality dimension of the at least one personality dimension is at least one of: extraversion, introversion, sensing, intuition, judging, thinking, feeling, openness, neuroticism, agreeableness, dating, work, interview, friendship, sex, or combinations thereof.

In some embodiments, the at least one processor displays at least one personalized recommendation on the at least one screen of the at least one computing device; wherein the at least one personalized recommendation is based on the at least one personality metric.

In some embodiments, the at least one personalized recommendation is further based on a particular situation.

In some embodiments, the particular situation comprises at least one of: a date, work, an interview, a party, or combinations thereof.

In some embodiments, the at least one processor analyzes at least one of: the facial expression of the at least one person or the appearance of the at least one person and optimizes at least one of: the facial expression of the at least one person or the appearance of the at least one person for the particular situation.

In some embodiments, an optimal score is indicated by "1" and a non-optimal score is indicated by "0".

In some embodiments, the at least one personalized recommendation is displayed on the at least one screen in the form of at least one module, wherein the at least one module comprises at least one of: at least one module for training personality changes, at least one module for personalized information, at least one module for personalized career guidance, at least one module for training personality changes, or combinations thereof.

In some embodiments, the at least one pscyhotype according to Briggs Myers is at least one of: INTJ, INTP, ENTJ, ENTP, INFJ, INFP, ENFJ, ENFP, ISTJ, ISFJ, ESTJ, ESFJ, ISTP, ISFP, ESTP, or ESFP.

In some embodiments, the at least one processor correlates the at least one pscyhotype according to Briggs Myers with the at least one personality trait according to the Big 5 to obtain at least one correlation; and the at least one processor displays the at least one correlation on the at least one screen of the at least one device.

In some embodiments, the at least one processor obtains the at least one compatibility score by: determining at least one personality metric of a first person, determining at least one personality metric of a second person, and comparing the at least one personality metric of the first person with the at least one personality metric of the second person.

In some embodiments, the at least one processor trains the PNN by: obtaining at least one neural network; obtaining at least one set of visual inputs; wherein each visual input of the at least one set of visual inputs comprises a face of at least one person; annotating the at least one set of visual inputs with at least one set of results of at least one personality test, thereby obtaining at least one set of annotated visual inputs; wherein each annotated visual input of the at least one set of annotated visual inputs comprises: the face of the at least one person, and the result of the at least one personality test corresponding to the at least one person;

and inputting the at least one set of annotated visual inputs into the at least one neural network, thereby obtaining at least one PNN.

In some embodiments, the at least one processor validates the PNN with at least a second set of annotated visual inputs.

In some embodiments, at least one of: the first set of annotated inputs or the second set of annotated visual inputs is annotated manually.

In some embodiments, the at least one set of visual inputs comprises at least one portrait image.

In some embodiments, the at least one visual input has an input resolution chosen from at least one of: 256×256, 512×512, 1024×1024, 2048×2048, 4096×4096, 640×480, 1280×720, 800×600, or combinations thereof.

In some embodiments, the at least one visual input has a color scheme chosen from at least one of: RGB, YCrCb, YCbCr, YUV, LAB, or combinations thereof.

In some embodiments, the at least one processor normalizes the at least one visual input.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

FIG. 3 illustrates an exemplary psychodiagnostic neural network (PNN) architecture which may be configured for determination of personality types.

FIG. 4 illustrates the exemplary inputs and outputs of the exemplary PNN shown in FIG. 3.

DESCRIPTION OF ILLUSTRATIVE EXAMPLES

Figure 1:
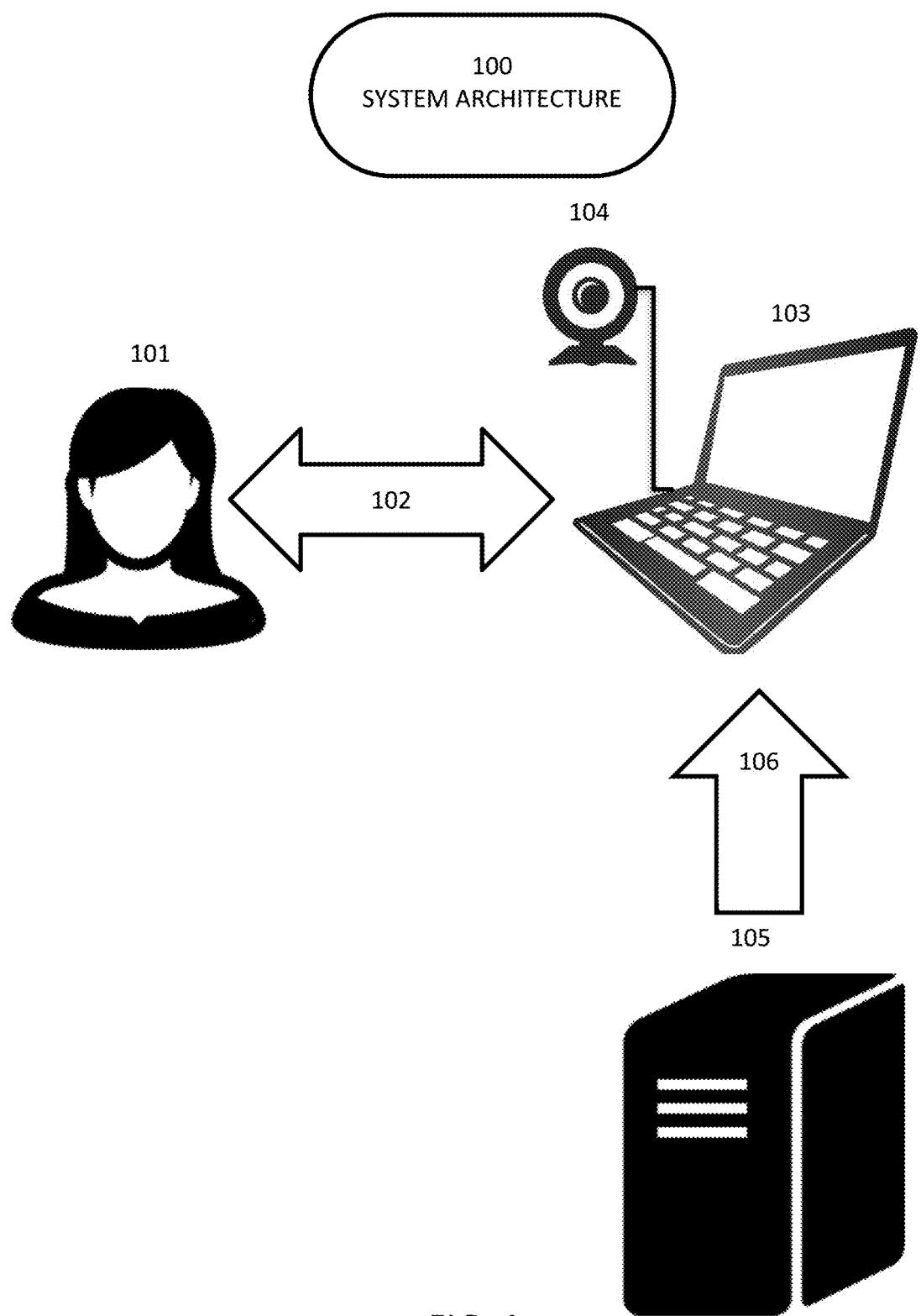
FIG. 1 illustrates an exemplary environment in accordance with at least some embodiments of the present disclosure.

Embodiments of the present disclosure, briefly summarized above and discussed in greater detail below, can be understood by reference to the illustrative embodiments of the disclosure depicted in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

Among those benefits and improvements that have been disclosed, other objects and advantages of this disclosure can become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the disclosure may be readily combined, without departing from the scope or spirit of the disclosure. Further, when a particular feature, structure, or characteristic is described in connection with an implementation, it is submitted that it is within the knowledge of one skilled in the art to affect such feature, structure, or characteristic in connection with other implementations whether or not explicitly described herein.

The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" means that events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, the disclosed specially programmed computing systems with associated devices are configured to operate in the distributed network environment, communicating over a suitable data communication network (e.g., the Internet, etc.) and utilizing at least one suitable data communication protocol (e.g., IPX/SPX, X.25, AX.25, AppleTalk™, TCP/IP (e.g., HTTP), etc.). Of note, the embodiments described herein may, of course, be implemented using any appropriate hardware and/or computing software languages. In this regard, those of ordinary skill in the art are well versed in the type of computer hardware that may be used, the type of computer programming techniques that may be used (e.g., object oriented programming), and the type of computer programming languages that may be used (e.g., C++, Objective-C, Swift, Java, Javascript). The aforementioned examples are, of course, illustrative and not restrictive.

As used herein, the terms "image(s)" and "image data" are used interchangeably to identify data representative of visual content which includes, but not limited to, images encoded in various computer formats (e.g., ".jpg", ".bmp," etc.), streaming video based on various protocols (e.g., Real-time Streaming Protocol (RTSP), Real-time Transport Protocol (RTP), Real-time Transport Control Protocol (RTCP), etc.), recorded/generated non-streaming video of various formats (e.g., ".mov," ".mpg," ".wmv," ".avi," ".flv," ect.), and real-time visual imagery acquired through a camera application on a mobile device.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

In another form, a non-transitory article, such as a non-transitory computer readable medium, may be used with any of the examples mentioned above or other examples except that it does not include a transitory signal per se. It does include those elements other than a signal per se that may hold data temporarily in a "transitory" fashion such as RAM and so forth.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor.

As used herein, the term "user" shall have a meaning of at least one user.

As used herein, the terms "face" and "head" are used interchangeably and both refer to any portion of a user's body situated above the user's shoulders. The terms "face" and "head" are meant to encompass any accessories worn by the user in the portion of the user's body above the shoulders including but not limited to, a hat, glasses, jewelry and the like.

As used herein, the term "psychodiagnostic" means "capable of determining at least one psychological, sexual, professional, social, spiritual, personality-related, or other like characteristic of at least one person."

As used herein, the term "psycho personality correction" means "at least one suggestion, recommendation, or the like, where the at least one suggestion, recommendation, or the like is based on at least one psychodiagnostic criteria."

The terms "psychotype" and "personality type" are synonymous and are used herein interchangeably.

The present disclosure presents, among other things, a solution to the technical problem of determining at least one aspect of personality based on at least one visual input.

In some embodiments, the present disclosure provides exemplary computer systems and computer implemented methods for estimating psychological characteristics of users and recommendations, that can help them to determine behaviors and suitable development paths, as disclosed further. In some embodiments, the disclosed system and method may assist in choosing the optimal model of behavior focusing on the unique capabilities and potential of the individual. In some embodiments, the disclosed system and method contributes to user introspection. In some embodiments, the disclosed system and method provides support and assistance in making decisions. In some embodiments, the disclosed system and method encourages the user. In some embodiments, the disclosed system and method helps the user to relax. In some embodiments, the disclosed system and method allows for prediction and tracking of personality changes. In some embodiments, the disclosed system and method helps the user to adjust the tactics of their behavior. In some embodiments, the disclosed system and method helps the user to plan daily activities. In some embodiments, the disclosed system and method contributes to the formation of the skills and abilities necessary for the optimal solution of the various tasks. In some embodiments, the disclosed system and method contributes to self-development. In some embodiments, the disclosed system and method helps to cope with the difficulties arising from interpersonal interaction.

In some embodiments, the disclosed computer systems and computer implemented methods may include several modules, as detailed further herein. In some embodiments the several modules can include at least one diagnostics module. In some embodiments the several modules can include at least one face scan module. In some embodiments the several modules can include at least one estimation of a psychotype according to the theory of Briggs Myers. In some embodiments, the several modules can include at least one module that provides psychotype descriptions and recommendations. In some embodiments the several modules can include at least one estimation of possible consensual opinion according to Big 5 criteria. In some embodiments the several modules can include at least one estimation of compatibility by six criteria (for example, "General", "Love", "Friendship", "Work", "Sex", "Family"). In some embodiments the several modules can include at least one estimation of the level of optimal appearance based on the first impression for the following situations (for example, "Date", "Work", "Interview", "Party"). In some embodiments the several modules can include at least one set of methods adapted for the mobile device for personality research. In some embodiments the several modules can include at least one sharing of results in social networks and instant messengers. In some embodiments the several modules can include at least one module for training personality changes. In some embodiments the several modules can include at least one personalized recommendation system. In some embodiments the several modules can include at least one information module (e.g., articles on topics of interest). In some embodiments the several modules can include at least one system for planning personal changes with daily tasks. In some embodiments the several modules can include at least one career guidance module with development plan in accordance with the profile of successful employees in the area of interest to the user.

In some embodiments, the disclosed computer systems and computer implemented methods allow users to find out more information about aspects of their personality, as well as get recommendations for personal development. In some embodiments, the user can find out information about themselves by means of visual diagnostics by taking one or several photographs with an electronic computing device camera, or uploading at least one picture or video. In some embodiments, electronic computing devices may be, without limitation, any electronic computing device at least includes and/or operationally associates with at least one another electronic computer device that includes at least one processor, a digital camera, and the disclosed software. For example, an exemplary electronic computing device may be at least one selected from the group of desktop, laptop, mobile device (e.g., tablet, smartphone, etc.), Internet-of-Things (IoT) device (e.g., smart thermostat), and the like.

In some embodiments, the disclosed computer systems and computer implemented methods allow the user to find out perceived personality traits in accordance with the Big Five personality traits (BIG 5); relate them to one of the 16 personality types in accordance with the theory of Isabel Briggs Myers. In some embodiments, the disclosed system provides detailed information about the user. In some embodiments, the user can check their compatibility with another person, according to a number of criteria: e.g., "General", "Love", "Friendship", "Work", "Sex", by taking a photograph or uploading it to their electronic computing device. In some embodiments, the user can be provided with the following recommendation: how much the first impression about them will be favorable for particular situations, e.g., "Dating", "Work", "Interview", "Party", and choose the optimal facial expression and appearance for these situations. For example, "0"—"unfavorable", "1"—"favorable". In some embodiments, the user may utilize questionnaires provided by the disclosed system to get additional information. Table 1 illustrates the exemplary questionnaire for the purposes as mentioned above.

As shown in Table 1, the preference estimate may consist of a letter indicating the "direction" of preference, and a number indicating the "strength" of preference. In some embodiments, the disclosed system may be configured to count the answers, provided by the user. For example, 1 or 2 points may be awarded for each answer, provided by the user. In some embodiments, the disclosed system determines the letter, comparing the scores for both alternatives, in accordance with the Table 1. For example, if E=17 and I=9, then E is dominant. Further, the disclosed system may subtract the smaller raw score from the larger one; record the difference; find the number in Table 1, corresponding to that difference; estimate of preference. For example, if the difference is 0, then priority is given to the INFP.

TABLE 1

Exemplary personality test.

| # | Question | Letter | Score | Answer |
|---|---|---|---|---|
| 1 | Which of these words do you like better: | E | 2 | (b) talkative |
| 1 | | I | 1 | (a) quiet |
| 2 | You'd rather be friends with someone who: | N | 1 | (a) has interesting ideas |
| 2 | | S | 1 | (b) is practical |
| 3 | When you are at a party you'd rather: | E | 1 | (a) participate in a group discussion |
| 3 | | I | 2 | (b) talk privately to someone you know |
| 4 | Which of these words do you like better: | N | 1 | (b) theoretical |
| 4 | | S | 2 | (a) factual |
| 5 | You have a hard time dealing with: | J | 1 | (b) frequent changes |
| 5 | | P | 1 | (a) routine |
| 6 | Which of these words do you like better: | E | 1 | (a) changing |
| 6 | | I | 2 | (b) steady |
| 7 | You are usually guided by | F | 1 | (a) emotion rather than reason |
| 7 | | T | 1 | (b) reason rather than emotion |
| 8 | Which of these words do you like better: | J | 2 | (b) solution |
| 8 | | P | 2 | (a) inspiration |
| 9 | You would rather: | J | 1 | (b) have everything go according to plan |
| 9 | | P | 1 | (a) encounter unexpected situations |
| 9 | Which of these words do you like better: | N | 1 | (b) ideal |
| 9 | | S | 2 | (a) real |
| 11 | How do you feel about making plans? | J | 1 | (a) anxious |
| 11 | | P | 1 | (b) neutral |
| 12 | Which of these words do you like better: | F | 1 | (a) charity |
| 12 | | T | 2 | (b) forecast |

TABLE 1-continued

Exemplary personality test.

| # | Question | Letter | Num | Answer |
|---|---|---|---|---|
| 13 | Which quality is more admirable: | N | 1 | (a) insightfulness |
| 13 | | S | 1 | (b) rationality |
| 14 | Which of these words do you like better: | J | 2 | (a) consistent |
| 14 | | P | 2 | (b) unexpected |
| 15 | Would you rather: | N | 1 | (b) design |
| 15 | | S | 2 | (a) build |
| 16 | Which of these words do you like better: | F | 2 | (b) empathize |
| 16 | | T | 2 | (a) investigate |
| 17 | Which of these words do you like better: | F | 1 | (b) gratitude |
| 17 | | T | 1 | (a) compensation |
| 18 | Which of these words do you like better: | F | 1 | (a) accepting |
| 18 | | T | 1 | (b) critical |
| 19 | Which of these words do you like better: | J | 2 | (a) controlled |
| 19 | | P | 2 | (b) unregulated |
| 20 | Which of these words do you like better: | F | 2 | (b) sentiment |
| 20 | | T | 2 | (a) argument |
| 21 | Following a plan is: | J | 2 | (a) reassuring |
| 21 | | P | 2 | (b) restrictive |
| 22 | When approaching a challenge you'd rather: | N | 1 | (b) find your own solution |
| 22 | | S | 1 | (a) use the most common solution |
| 23 | Meeting new people is: | E | 1 | (a) exciting |
| 23 | | I | 1 | (b) exhausting |
| 24 | You'd rather be called: | F | 1 | (a) a passionate person |
| 24 | | T | 2 | (b) a reasonable person |
| 25 | Normally you are: | E | 2 | (a) open and expressive |
| 25 | | I | 2 | (b) calm and composed |
| 26 | Would you say that: | E | 1 | (a) you are more enthusiastic than others |
| 26 | | I | 1 | (b) you are less enthusiastic than others |
| 27 | When you think of something to do later: | J | 1 | (b) you write it down |
| 27 | | P | 1 | (a) you forget about it until comes up again |
| 28 | You'd rather be friends with: | N | 1 | (a) someone who is bursting with fresh ideas |
| 28 | | S | 2 | (b) someone who is down to earth |
| 29 | You like to: | N | 2 | (b) invent new things |
| 29 | | S | 2 | (a) achieve a predictable outcome |
| 30 | When you have an important task you'd rather: | J | 1 | (a) plan everything out |
| 30 | | P | 2 | (b) jump in and figure it out as you go |
| 31 | When communicating with others: | E | 2 | (a) you can talk to anyone for any length of time |
| 31 | | I | 2 | (b) you reserve lengthy conversations for people and situations that matter |
| 32 | Which of these words do you like better: | N | 1 | (b) figurative |
| 32 | | S | 1 | (a) literal |
| 33 | If you were a university instructor you'd teach: | N | 2 | (b) philosophy |
| 33 | | S | 2 | (a) math |
| 34 | Which of these words do you like better: | E | 1 | (a) outgoing |
| 34 | | I | 1 | (b) reserved |
| 35 | When out with friends you'd rather: | E | 1 | (a) be the center of attention and have everyone follow you |
| 35 | | I | 2 | (b) let everyone do whatever they want |
| 36 | Which of these words do you like better: | F | 2 | (b) sensing |
| 36 | | T | 2 | (a) analysing |
| 37 | In a group of people it's more common to see you: | E | 2 | (a) introducing people to each other |
| 37 | | I | 1 | (b) be introduced to others |
| 38 | Which of these words do you like better: | F | 1 | (a) friendly |
| 38 | | T | 2 | (b) firm |
| 39 | Knowing in advance that you'll have to do something on a certain date is: | J | 1 | (a) great, it's easier to make plans |
| 39 | | P | 1 | (b) inconvenient, it limits your freedom |
| 40 | Which of these words do you like better: | F | 2 | (b) compassion |
| 40 | | T | 1 | (a) principle |

FIG. 1 illustrates an exemplary environment 100 in accordance with at least some embodiments of the present disclosure. As shown in FIG. 1, environment 100 may include a user 101, a computer or mobile device 103, a camera 104 and a server 105. Other devices may also be included. The computer 103 may include any appropriate type of computers, such as desktops, laptops, mobile devices, such as, but not limited to, mobile phones, smartphones and tablets, or any other similarly suitable devices. The exemplary camera 104 may be a built-in camera, or an external camera or any other suitable camera. Further, the server 105 may include any appropriate type of server computer or a plurality of server computers. The user 101 may interact 102 with the computer 103 and the camera 104. The camera 104 continuously tracks the user activity in accordance with one ore principles of the present disclosure as detailed herein. The user 101 may be a single user or a plurality of users. The computer 103 and the server 105 may be implemented on any appropriate computing circuitry platform as detailed herein.

Figure 2:
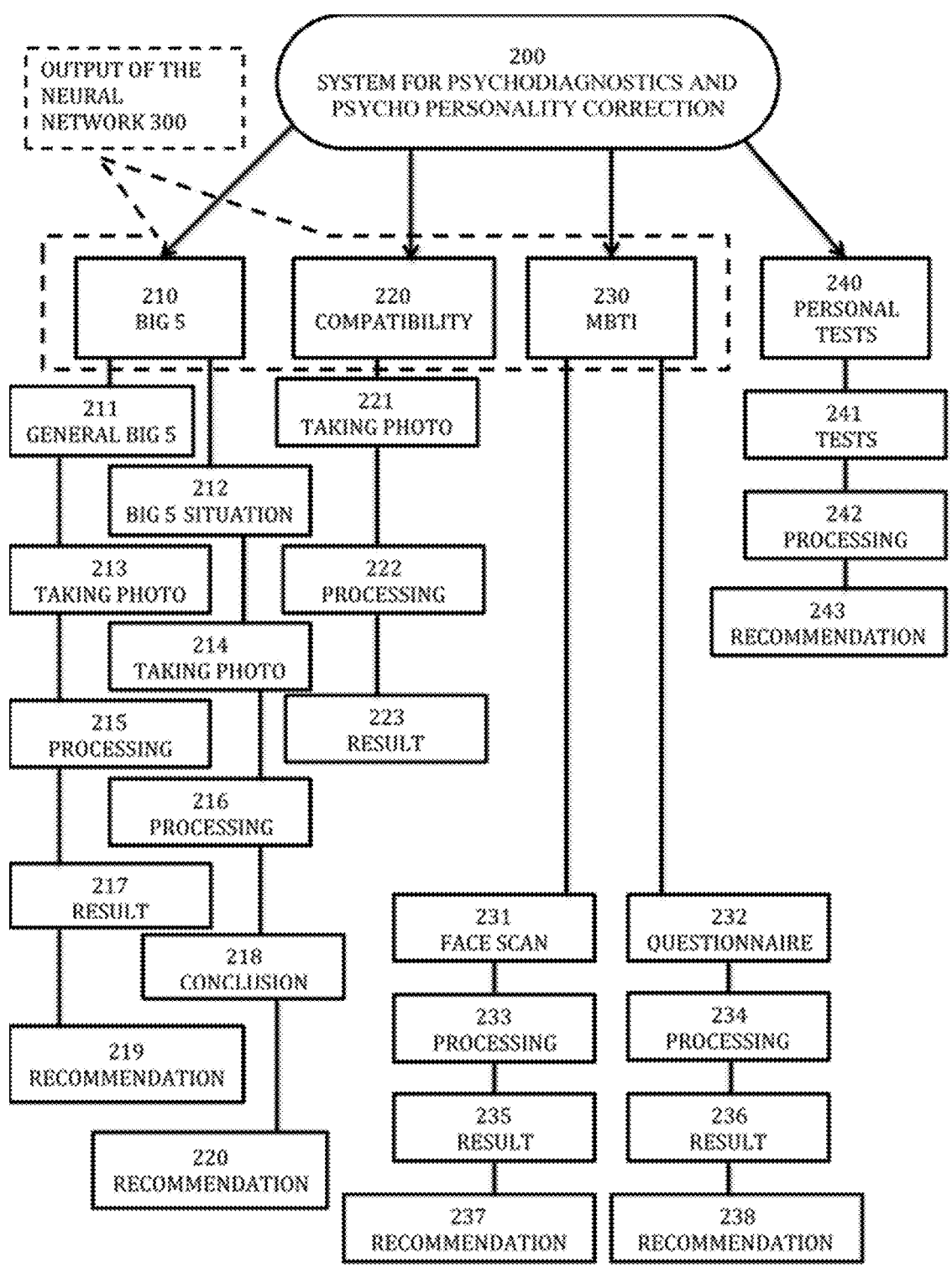
FIG. 2 illustrates am exemplary scheme of the disclosed computer system and computer implemented methods for psychodiagnostics and psycho personality correction.

FIG. 2 illustrates the exemplary scheme of the disclosed computer system and computer implemented methods for psychodiagnostics and psycho personality correction 200. As shown in FIG. 2, in some embodiments, as detailed herein, the exemplary disclosed system may include the following modules: BIG 5 (210), compatibility (220), MBTI (230) and personal tests (240). The modules 210, 220, and 230 are parts of the diagnostics module of the disclosed system and may be based on the results obtained utilizing the neural network, as detailed in FIG. 3. In some embodiments, the disclosed system may prompt the user to take a portrait photograph. In some embodiments, the user may upload a portrait photograph. The photograph is analyzed and the user receives personalized information about perceived traits in accordance with the five criteria of BIG 5, or/and the 16 types of MBTI. The examples of the BIG 5 criteria may be: openness, conscientiousness, extraversion, agreeableness, neuroticism. The examples of MBTI types may be: ISTJ— the duty fulfiller, ISTP—the mechanic, ISFJ—the nurturer, ISFP—the artist, INFJ—the protector, INFP—the idealist, INTJ—the scientist, INTP—the thinker, etc. In some embodiments, in order to determine the type of personality according to MBTI, the following correlations between the BIG 5 types (openness, conscientiousness, extraversion, agreeableness) and the MBTI types have been utilized: corr(openness, N)=0.22; corr(conscientiousness, J)=0.32; corr(extraversion, E)=0.33; corr(agreeableness, F)=0.39.

In some embodiments of the present disclosure, the basis for the visual diagnosis of MBTI personality types is the BIG 5 personality assessment system. The exemplary neural network architecture configured for estimation of BIG 5 types is disclosed in FIG. 3.

Referring to FIG. 2, the user may use questionnaires (232) to refine their MBTI result. An exemplary questionnaire is disclosed in Table 1. The submodule BIG 5 situation (212) may provide the user with the estimation how others could perceive them, in certain situations, for example, "Work", "Interview", "Party", "Date". In some embodiments, for each situation, the disclosed algorithm choses a set of criteria: if the first impression according to these criteria is greater than the median, the user receives a message that the estimated impression about them is optimal for the given situation; otherwise, that it is not optimal. For example, the following factors should be above the median: situation "Dating": extraversion, openness, emotional stability; situation "Work": conscientiousness, openness, emotional stability, agreeableness; situation "Interview": conscientiousness, openness, emotional stability, extraversion, situation "Party": extraversion, agreeableness.

In some embodiments, the compatibility module (220) allows to check compatibility between two users. The disclosed system and method may process images of two users taken either in the real-time or uploaded to the electronic computing device. For example, in order to determine the compatibility, personal similarities can be estimated based on the MBTI criteria: 4 matches from 92% to 100%; 3 matches from 84% to 91%; 2 matches from 72% to 83%; 1 match from 60% to 72%; 0 matches from 40% to 59%.

In some embodiments, the compatibility is estimated in the six categories: "General", "Love", "Friendship", "Work", "Sex", "Family".

Personal tests (240) may be any tests (for example, as disclosed in Table 1) based on classical psychological theories and adapted for a mobile application. In some embodiments such tests may include at least some of the following: study of imagination, study of perception, study of speech, study of attention, study of memory, study of sensations, study of thinking, study of intelligence, study of creativity, study of abilities, study of emotional and volitional processes, study of aggression, study of anxiety, study of depression, study of neurosis, study of family relationships, motivation research, vocational orientation research, interpersonal relations research, etc.

FIG. 3 illustrates an exemplary psychodiagnostic neural network (PNN) architecture 200 which may be configured for determination of BIG 5, MBTI and related types, as disclosed further. As shown in FIG. 3, an exemplary PNN may be based on the DenseNet-121, DenseNet-169, DenseNet-201, DenseNet-264, or any other suitable neural network architecture. In some embodiments, the exemplary PNN is initially trained on at least one first dataset of at least 100,000 images. In some embodiments, the PNN is then trained on at least one second dataset of 12,000 annotated images. In other embodiments, datasets of various (i.e., larger or smaller) sizes may be used for such purposes, starting with at least 4000 samples. For validation, 4 000 annotated samples may be used. In some embodiments, datasets of 1 . . . N samples may be used for validation, where N is any number of samples in the training dataset. In some embodiments, each sample of both exemplary training and validation subsets can manually annotated according to BIG 5 criteria. In some embodiments, to get an averaged group opinion, at least 30 estimations may be made for each image. In other embodiments, the number of estimations may range from 30 to 100.

In some embodiments, the exemplary architecture of the neural network utilized for BIG 5 predictions may be:
DenseNet121 (input: 224×224×3);
Dropout (0.5);
Dense (6, activation='linear').

In some embodiments, the exemplary training steps of the neural network utilized for BIG 5 predictions may be:
def ClassificationModel (n_classes=6, input_shape=(224, 224,3)):
  base_model=DenseNet121(weights=None, include_top=False, input_shape=input_shape)
  x=AveragePooling2D(pool_size=(3,3), name='avg_pool')(base_model.output)
  x=Flatten( )(x)
  x=Dense(1024, activation='relu', name='densepostpool') (x)
  x=Dropout(0.5)(x)
  output=Dense(n_classes, activation='sigmoid', name='predictions')(x)
  model=Model(inputs=base_model.input, output=output)
  return model In some embodiments, the Dropout layers may be used, with the rate parameter 0.25-0.75. In some embodiments, activation functions "sigmoid", "relu", "leaky rely" may be used for the Dense layers. In some embodiments, Average-Pooling layers may be used with the pool size of (3,3), (4,4), (5,5), (6,6). In other embodiments, MaxPooling layers may be used instead of AveragePooling layers.

For example, the dataset used for the initial training procedure may be ImageNet (http://www.image-net.org). In other embodiments, other datasets may be used for such purposes, for example, MS-COCO (http://cocodataset.org), Open Images Dataset (https://github.com/openimages/dataset), VQA Dataset (https://visualqa.org), etc. In some embodiments, for example, the loss function may be mean absolute error. In other embodiments, the loss function may be square loss, hinge loss, logistic loss, cross entropy loss. In some embodiments, for example, the input resolution may be 224×224×3. In other embodiments, the image resolutions may be 256×256, 512×512, 1024×1024, 2048×2048, 4096× 4096, 640×480, 1280×720, 800×600. In some embodiments, for example, the color scheme may be RGB. In other embodiments, the color schemes may be YCrCb, YCbCr, YUV, Lab.

In some embodiments, the exemplary neural network may produce the following classes: agreeableness, conscientiousness, extraversion, interview, neuroticism, openness; each value may range from 0 to 1. In some embodiments, the exemplary training metrics may be: {'loss': 0.0495771, 'mean_absolute_error': 0.1763407}. In some embodiments, the exemplary thresholds for exemplary training dataset may be: 0 if class probability <0.4; 1 if class probability >0.6. In other embodiments, the thresholds may be [0.5, 0.5], [0.45, 0.55], [0.35, 0.65], [0.3, 0.7], [0.25, 0.75], [0.2, 0.8].

In some embodiments, the normalization of input images (e.g., RGB images) may be done in the following way: $x=(x-mean(x))/standard\_deviation(x)$. In some embodiments, the normalization of input images may be done in the following way: $x=(x-min(x))/(max(x)-min(x))$. In some embodiments, the normalization of input RGB images may be done in the following way: $x=(x-mean(x))/(max(x)-min(x))$.

For example, the output of the neural network may be:
agreeableness=0.8516142826598246;
conscientiousness=0.8922540381791483;
extraversion=0.8426874231872183;
interview=0.8607540702656384;
neuroticism=0.8239382239382239;
openness=0.8717855849329953.

FIG. 4 illustrates exemplary inputs and outputs of the exemplary neural network shown in FIG. 3.

At least some aspects of the present disclosure will now be described with reference to the following numbered clauses hereinafter designated as [C1, C2, C3, C4 . . . ]

C1: A computer-implemented method, comprising: obtaining, by at least one processor, at least one visual input comprising a face of at least one person; inputting, by the at least one processor, the at least one visual input into at least one psychodiagnostic neural network (PNN) to obtain at least one personality metric of the at least one person; wherein the at least one personality metric of the at least one person comprises: at least one personality dimension, and at least one numerical personality score wherein the at least one numerical personality score provides a numerical indication of the strength of a particular personality dimension; and displaying at least one personality report on at least one screen of at least one computing device; wherein the at least one personality report comprises the at least one personality metric of the at least one person.

C2: The method of C1, wherein the at least one visual input comprises at least one video frame, at least one image, or both.

C3: The method of C1 or C2, wherein a particular personality metric of the at least one personality metric is at least one of: at least one psychotype according to Briggs Myers, at least one personality trait according to the Big 5, a compatibility score, a score evaluating the at least one person in a particular situation, or a combination thereof.

C4: The method of any of C1-C3 wherein a particular personality dimension of the at least one personality dimension is at least one of: extraversion, introversion, sensing, intuition, judging, thinking, feeling, openness, neuroticism, agreeableness, dating, work, interview, friendship, sex, or combinations thereof.

C5: The method any of C1-C4, further comprising, by the at least one processor, displaying at least one personalized recommendation to the at least one screen of the at least one computing device; wherein the at least one personalized recommendation is based on the at least one personality metric.

C6: The method of C4, wherein the at least one personalized recommendation is further based on a particular situation.

C7: The method of C6, wherein the particular situation comprises at least one of: a date, work, an interview, a party, or combinations thereof.

C8: The method of C7, further comprising, by the at least one processor: analyzing at least one of: the facial expression of the at least one person or the appearance of the at least one person; and optimizing at least one of: the facial expression of the at least one person or the appearance of the at least one person for the particular situation.

C9: The method of C8, wherein an optimal score is indicated by "1" and a non-optimal score is indicated by "0".

C10: The method of C5, wherein the at least one personalized recommendation is displayed on the at least one screen in the form of at least one module, wherein the at least one module comprises at least one of: at least one module for training personality changes, at least one module for personalized information, at least one module for personalized career guidance, at least one module for training personality changes, or combinations thereof.

C11: The method of C3, wherein the at least one psychotype according to Briggs Myers is at least one of: INTJ, INTP, ENTJ, ENTP, INFJ, INFP, ENFJ, ENFP, ISTJ, ISFJ, ESTJ, ESFJ, ISTP, ISFP, ESTP, or ESFP.

C12: The method of C3, further comprising: by the at least one processor, correlating the at least one psychotype according to Briggs Myers with the at least one personality trait according to the Big 5 to obtain at least one correlation; and by the at least one processor, displaying the at least one correlation on the at least one screen of the at least one device.

C13: The method of C3, wherein the at least one compatibility score is obtained by: by the at least one processor, determining at least one personality metric of a first person; by the at least one processor, determining at least one personality metric of a second person; by the at least one processor, comparing the at least one personality metric of the first person with the at least one personality metric of the second person.

C14: The method of any of C1 to C13, wherein the at least one PNN is trained by: obtaining, by the at least one processor, at least one neural network, obtaining, by the at least one processor, at least one set of visual inputs; wherein each visual input of the at least one set of visual inputs comprises a face of at least one person; annotating, by the at least one processor, the at least one set of visual inputs with at least one set of results of at least one personality test, thereby obtaining at least one set of annotated visual inputs; wherein each annotated visual input of the at least one set of annotated visual inputs comprises: the face of the at least one person, and the result of the at least one personality test corresponding to the at least one person; and inputting the at least one set of annotated visual inputs into the at least one neural network, thereby obtaining at least one PNN.

C15: The method of C14, further comprising, by the at least one processor, validating the PNN with at least a second set of annotated visual inputs.

C16: The method of C15, wherein at least one of: the first set of annotated inputs or the second set of annotated visual inputs is annotated manually.

C17: The method of C14, wherein the at least one set of visual inputs comprises at least one portrait image.

C18: The method of C14, wherein the at least one visual input has an input resolution chosen from at least one of: 256×256, 512×512, 1024×1024, 2048×2048, 4096×4096, 640×480, 1280×720, 800×600, or combinations thereof.

C19: The method of C14, wherein the at least one visual input has a color scheme chosen from at least one of: RGB, YCrCb, YCbCr, YUV, LAB, or combinations thereof.

C20: The method of claim 14, further comprising, by the at least one processor, normalizing the at least one visual input.

C21: A system comprising: a camera component, wherein the camera component is configured to acquire at least one visual input comprising a face of at least one person; at least one processor; a non-transitory computer memory, storing a computer program that, when executed by the at least one processor, causes the at least one processor to: input the at least one visual input into at least one psychodiagnostic neural network (PNN) to obtain at least one personality metric of the at least one person; wherein the at least one personality metric of the at least one person comprises: at least one personality dimension, and at least one numerical personality score, wherein the at least one numerical personality score provides a numerical indication of the strength of a particular personality dimension; and display at least one personality report on at least one screen of at least one computing device; wherein the at least one personality report comprises the at least one personality metric of the at least one person.

C22: The system of C21, wherein the at least one visual input comprises at least one video frame, at least one image, or both.

C23: The system of C21 or C22, wherein a particular personality metric of the at least one personality metric is at least one of: at least one psychotype according to Briggs Myers, at least one personality trait according to the Big 5, a compatibility score, a score evaluating the at least one person in a particular situation, or a combination thereof.

C24: The system of any of C21 to C23, wherein a particular personality dimension of the at least one personality dimension is at least one of: extraversion, introversion, sensing, intuition, judging, thinking, feeling, openness, neuroticism, agreeableness, dating, work, interview, friendship, sex, or combinations thereof.

C25: The system of any of C21 to C24, wherein the at least one processor displays at least one personalized recommendation on the at least one screen of the at least one computing device; wherein the at least one personalized recommendation is based on the at least one personality metric.

C26: The system of C24, wherein the at least one personalized recommendation is further based on a particular situation.

C27: The system of C26, wherein the particular situation comprises at least one of: a date, work, an interview, a party, or combinations thereof.

C28: The system of C27, further wherein the at least one processor: analyzes at least one of: the facial expression of the at least one person or the appearance of the at least one person; and optimizes at least one of: the facial expression of the at least one person or the appearance of the at least one person for the particular situation.

C29: The system of C28, wherein an optimal score is indicated by "1" and a non-optimal score is indicated by "0".

C30: The system of C25, wherein the at least one personalized recommendation is displayed on the at least one screen in the form of at least one module, wherein the at least one module comprises at least one of: at least one module for training personality changes, at least one module for personalized information, at least one module for personalized career guidance, at least one module for training personality changes, or combinations thereof.

C31: The system of C23, wherein the at least one pscyhotype according to Briggs Myers is at least one of: INTJ, INTP, ENTJ, ENTP, INFJ, INFP, ENFJ, ENFP, ISTJ, ISFJ, ESTJ, ESFJ, ISTP, ISFP, ESTP, or ESFP.

C32: The system of C23, wherein the at least one processor correlates the at least one pscyhotype according to Briggs Myers with the at least one personality trait according to the Big 5 to obtain at least one correlation; and wherein the at least one processor displays the at least one correlation on the at least one screen of the at least one device.

C33: The system of C23, wherein the at least one processor obtains the at least one compatibility score by: determining at least one personality metric of a first person. at least one personality metric of a second person. And comparing the at least one personality metric of the first person with the at least one personality metric of the second person.

C34: The system of any of C21 to C33, wherein the at least one processor trains the PNN by: obtaining at least one neural network, obtaining at least one set of visual inputs; wherein each visual input of the at least one set of visual inputs comprises a face of at least one person; annotating the at least one set of visual inputs with at least one set of results of at least one personality test, thereby obtaining at least one set of annotated visual inputs; wherein each annotated visual input of the at least one set of annotated visual inputs comprises: the face of the at least one person, and the result of the at least one personality test corresponding to the at least one person; and inputting the at least one set of annotated visual inputs into the at least one neural network, thereby obtaining at least one PNN.

C35: The system of C34, wherein the at least one processor validates the PNN with at least a second set of annotated visual inputs.

C36: The system of C35, wherein at least one of: the first set of annotated inputs or the second set of annotated visual inputs is annotated manually.

C37: The system of C34, wherein the at least one set of visual inputs comprises at least one portrait image.

C38: The system of C24, wherein the at least one visual input has an input resolution chosen from at least one of: 256×256, 512×512, 1024×1024, 2048×2048, 4096×4096, 640×480, 1280×720, 800×600, or combinations thereof.

C39: The system of C24, wherein the at least one visual input has a color scheme chosen from at least one of: RGB, YCrCb, YCbCr, YUV, LAB, or combinations thereof.

C40: The system of C24, wherein the at least one processor, normalizes the at least one visual input.

While a number of embodiments of the present disclosure have been described, it is understood that these embodiments are illustrative only, and not restrictive, and that many modifications may become apparent to those of ordinary skill in the art, including that various embodiments of the disclosed methodologies, the disclosed systems, and the disclosed devices described herein can be utilized in any combination with each other. Further still, the various steps may be carried out in any desired order (and any desired steps may be added and/or any desired steps may be eliminated).

The invention claimed is:

1. A computer-implemented method, comprising:
   obtaining, by at least one processor, at least one neural network, obtaining, by the at least one processor, at least one set of visual inputs;
   wherein each visual input of the at least one set of visual inputs comprises a face of at least one person;
   annotating, by the at least one processor, the at least one set of visual inputs with at least one set of results of at least one personality test, thereby obtaining at least one set of annotated visual inputs;
   wherein each annotated visual input of the at least one set of annotated visual inputs comprises:
   the face of the at least one person, and
   the result of the at least one personality test corresponding to the at least one person;
   inputting the at least one set of annotated visual inputs into the at least one neural network, thereby obtaining at least one psychodiagnostic neural network (PNN);
   obtaining, by the at least one processor, at least one additional visual input comprising a face of at least one person;
   inputting, by the at least one processor, the at least one additional visual input into the at least one PNN, so as to obtain at least one personality metric of the at least one person of the at least one additional visual input;
   wherein the at least one personality metric of the at least one person of the at least one additional visual input comprises:
   at least one personality dimension of the at least one person of the at least one additional visual input, and
   at least one numerical personality score of the at least one person of the at least one additional visual input,
   wherein the at least one numerical personality score provides a numerical indication of the strength of the at least one personality dimension; and
   displaying at least one personality report on at least one screen of at least one computing device;
   wherein the at least one personality report comprises the at least one personality metric of the at least one person of the at least one additional visual input.

2. The method of claim 1, wherein each visual input of the at least one set of visual inputs, the at least one additional visual input, or any combination thereof comprises at least one video frame, at least one image, or both.

3. The method of claim 1, wherein the at least one personality metric is at least one of: at least one psychotype according to Briggs Myers, at least one personality trait according to the Big 5, a compatibility score, a score evaluating the at least one person in a particular situation, or a combination thereof.

4. The method of claim 1, wherein the at least one personality dimension is at least one of: extraversion, introversion, sensing, intuition, judging, thinking, feeling, openness, neuroticism, agreeableness, dating, work, interview, friendship, sex, or combinations thereof.

5. The method of claim 1, further comprising, by the at least one processor, displaying at least one personalized recommendation to the at least one screen of the at least one computing device; wherein the at least one personalized recommendation is based on the at least one personality metric.

6. The method of claim 5, wherein the at least one personalized recommendation is further based on a particular situation.

7. The method of claim 6, wherein the particular situation comprises at least one of: a date, work, an interview, a party, or combinations thereof.

8. The method of claim 7, further comprising, by the at least one processor:
   analyzing at least one of: the facial expression of the at least one person or the appearance of the at least one person; and
   optimizing at least one of: the facial expression of the at least one person or the appearance of the at least one person for the particular situation.

9. The method of claim 8, wherein an optimal score is indicated by "1" and a non-optimal score is indicated by "0".

10. The method of claim 5, wherein the at least one personalized recommendation is displayed on the at least one screen in the form of at least one module, wherein the at least one module comprises at least one of: at least one module for training personality changes, at least one module for personalized information, at least one module for personalized career guidance, at least one module for training personality changes, or combinations thereof.

11. The method of claim 3, wherein the at least one pscyhotype according to Briggs Myers is at least one of: INTJ, INTP, ENTJ, ENTP, INFJ, INFP, ENFJ, ENFP, ISTJ, ISFJ, ESTJ, ESFJ, ISTP, ISFP, ESTP, or ESFP.

12. The method of claim 3, further comprising:
   by the at least one processor, correlating the at least one pscyhotype according to Briggs Myers with the at least one personality trait according to the Big 5 to obtain at least one correlation; and
   by the at least one processor, displaying the at least one correlation on the at least one screen of the at least one device.

13. The method of claim 3, wherein the at least one compatibility score is obtained by:
   by the at least one processor, determining at least one personality metric of a first person;
   by the at least one processor, determining at least one personality metric of a second person;
   by the at least one processor, comparing the at least one personality metric of the first person with the at least one personality metric of the second person.

14. The method of claim 1, further comprising, by the at least one processor, validating the at least one PNN, as obtained during the inputting step, with at least a second set of annotated visual inputs.

15. The method of claim 14, wherein at least one of: the set of annotated inputs or the second set of annotated visual inputs is annotated manually.

16. The method of claim 1, wherein the at least one set of visual inputs comprises at least one portrait image.

17. The method of claim 1, wherein each visual input of the set of visual inputs, the at least one additional visual input, or any combination thereof has an input resolution chosen from at least one of: 256×256, 512×512, 1024×1024, 2048×2048, 4096×4096, 640×480, 1280×720, 800×600, or combinations thereof.

18. The method of claim 1, wherein each visual input of the set of visual inputs, the at least one additional visual input, or any combination thereof has a color scheme chosen from at least one of: RGB, YCrCb, YCbCr, YUV, LAB, or combinations thereof.

19. The method of claim 1, further comprising, by the at least one processor, normalizing each visual input of the set of visual inputs, normalizing the at least one additional visual input, or any combination thereof.

20. A system comprising:
a camera component, wherein the camera component is configured to acquire at least one visual input comprising a face of at least one person,
at least one processor;
a non-transitory computer memory, storing a computer program that, when executed by the at least one processor, causes the at least one processor to:
obtain at least one neural network,
obtain at least one set of visual inputs;
wherein each visual input of the at least one set of visual inputs comprises a face of at least one person;
annotate the at least one set of visual inputs with at least one set of results of at least one personality test, thereby obtaining at least one set of annotated visual inputs;
wherein each annotated visual input of the at least one set of annotated visual inputs comprises:
the face of the at least one person, and the result of the at least one personality test corresponding to the at least one person; and
input the at least one set of annotated visual inputs into the at least one neural network, so as to obtain at least one psychodiagnostic neural network (PNN);
obtain, at least one additional visual input comprising a face of at least one person;
input the at least one additional visual input into the at least one PNN, so as to obtain at least one personality metric of the at least one person of the at least one additional visual input;
wherein the at least one personality metric of the at least one person of the at least one additional visual input comprises:
at least one personality dimension of the at least one person of the at least one additional visual input, and
at least one numerical personality score, of the at least one person of the at least one additional visual input wherein the at least one numerical personality score provides a numerical indication of the strength of the at least one personality dimension; and
display at least one personality report on at least one screen of at least one computing device;
wherein the at least one personality report comprises the at least one personality metric of the at least one person of the at least one additional visual input.

* * * * *